(12) United States Patent
Kozuki

(10) Patent No.: US 8,574,606 B2
(45) Date of Patent: Nov. 5, 2013

(54) LIQUID AGROCHEMICAL COMPOSITION CONTAINING HYDROPHOBIC AGROCHEMICAL ACTIVE COMPOUND

(75) Inventor: Yumiko Kozuki, Takarazuka (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 77 days.

(21) Appl. No.: 12/010,864

(22) Filed: Jan. 30, 2008

(65) Prior Publication Data

US 2008/0182755 A1 Jul. 31, 2008

(30) Foreign Application Priority Data

Jan. 31, 2007 (JP) ................................ 2007-021176

(51) Int. Cl.
*A01N 25/02* (2006.01)
*A01N 25/30* (2006.01)
(52) U.S. Cl.
USPC ............................ 424/405; 514/772; 514/975
(58) Field of Classification Search
None
See application file for complete search history.

(56) References Cited

U.S. PATENT DOCUMENTS

| 2003/0083201 A1 | 5/2003 | Kobayashi |
| 2006/0180677 A1 | 8/2006 | McManic et al. |
| 2006/0257440 A1 | 11/2006 | Asai et al. |

FOREIGN PATENT DOCUMENTS

| JP | 2003-89603 | 3/2003 |
| JP | 2003-128501 | 5/2003 |

OTHER PUBLICATIONS

UK Search Report issued Jun. 2, 2008 in connection with British Application No. GB0801707.1 corresponding to the present US Application.
Database WPI Section Ch, Week 200354 Thomson Scientific, London, GB; AN 2003-572654 XP 002592537 for JP 2003-089603, published Mar. 28, 2003.
English Abstract from Patent Abstracts of Japan for JP 2003-089603, published Mar. 28, 2003.
Search Report and Written Opinion issued Oct. 6, 2010 in Turkish Patent Application No. 2008/00351 corresponding to present US Application.
Office Action dated Aug. 31, 2011 issued in the corresponding Chinese Application No. 200810009563.1 together with English translation thereof.
Notification of Reasons for Refusal issued Feb. 21, 2012 in corresponding Japanese Patent Application No. 2007-021176, with English Translation.
Examination Report dated Oct. 4, 2012 in corresponding Turkish Application No. 2008/00351 (in the English language).
Office Action issued Jul. 26, 2012 in corresponding Australian Application No. 2008200454.
Office Action issued Oct. 16, 2012 in corresponding Taiwanese Application No. 097103413 (with English translation).

*Primary Examiner* — Abigail Fisher
*Assistant Examiner* — Frank Choi
(74) *Attorney, Agent, or Firm* — Wenderoth, Lind & Ponack, L.L.P.

(57) ABSTRACT

There is provided a liquid agrochemical composition having a stable water-diluted state, which comprises 0.5 to 30% by weight of one or more hydrophobic agrochemical active compounds, 1 to 20% by weight of one or more nonionic surfactants selected from the group consisting of a polyoxyethylene polyoxypropylene block copolymer and the like, 0 to 10% by weight of one or more anionic surfactant, 6 to 60% by weight of γ-butyrolactone, and 20 to 75% by weight of 1,3-dimethyl-2-imidazolidinone; and water-diluted solution obtained by diluting the liquid agrochemical composition with a 10 to 10,000-fold amount of water.

5 Claims, No Drawings

LIQUID AGROCHEMICAL COMPOSITION CONTAINING HYDROPHOBIC AGROCHEMICAL ACTIVE COMPOUND

BACKGROUND OF THE INVENTION

The present invention relates to a liquid agrochemical composition containing a hydrophobic agrochemical active compound.

Representative examples of a liquid agrochemical preparation containing a hydrophobic agrochemical active compound include emulsions and flowables. When emulsions or flowables are sprayed, they are used as a water-diluted solution by diluting with a large amount of water. In such a water-diluted solution, a hydrophobic agrochemical active compound is such that fine oil droplets or solid particles are dispersed in water by the action of a surfactant, and since this state is a thermodynamically unstable state, oil droplets containing the hydrophobic agrochemical active compound are separated with time and, when the hydrophobic agrochemical active compound is a solid, solid particles are precipitated and settled in some cases.

JP 2003-128501 A describes a liquid agrochemical preparation containing quizalofop-p-ethyl, which is a hydrophobic agrochemical compound, polyoxyethylenestyryl phenyl ether, dodecylbenzene sulfonic acid salt, Solvesso 200 and 1,3-dimethyl-2-imidazolidinone, but the liquid agrochemical preparation is not necessarily stable in the water-diluted state.

SUMMARY OF THE INVENTION

Under there circumstances, the present inventors have studied in order to obtain a liquid agrochemical preparation containing a hydrophobic agrochemical active compound which is stable in a water-diluted state. As a result, they have completed the present invention.

That is, the present invention provides:

(1) A liquid agrochemical composition comprising
   0.5 to 30% by weigh of one or more hydrophobic agrochemical active compounds;
   1 to 20% by weight of one or more nonionic surfactants selected from the following group (A);
   0 to 10% by weight of one of more anionic surfactants;
   6 to 60% by weight of γ-butyrolactone; and
   20 to 75% by weight of 1,3-dimethyl-2-imidazolidinone,
   the group (A):
   polyoxyethylene polyoxypropylene block copolymer,
   polyoxyethylene polyoxypropylene alkyl ether,
   polyoxyethylene polyoxypropylene alkyl phenol,
   polyoxyethylene polyoxypropylene polystyryl phenyl ether,
   and polyoxyethylene polyoxypropylene castor oil;

(2) The liquid agrochemical composition according to the above (1), wherein the nonionic surfactant is a polyoxyethylene polyoxypropylene block copolymer;

(3) The liquid agrochemical composition according the above (1) or (2), wherein an amount of the anionic surfactant is in a range of 1 to 10% by weight;

(4) The liquid agrochemical composition according to the above (3), wherein the anionic surfactant is an alkylbenzenesulfonate; and (5) A water-diluted solution, which is obtained by diluting the liquid agrochemical composition according to any one of the above (1) to (4) with a 10 to 10,000-fold amount of water.

The liquid agrochemical composition of the present invention (hereinafter, sometimes, referred to as the present liquid agrochemical composition) is stable in a water-diluted state.

DETAILED DESCRIPTION OF THE PREFERRED EMBODIMENTS

In the present invention, the hydrophobic agrochemical active compound means an agrochemical active compound which is insoluble or hardly soluble in water, and has solubility in water when water at 25° C. is used, of usually not higher than 0.5 g/L, preferably not higher than 0.1 g/L, and may have any form of a solid or a liquid at 25° C.

Examples of the agrochemical active compound include a herbicidal active compound, a fungicidal active compound, an insecticidal (acaricidal) active compound, and a plant growth controlling compound and, for example, the following compounds can be specifically exemplified.

As the herbicidal active compound, examples include dicarboxyimide herbicidal active compound: Flumiclorac-pentyl [herbicidal compound 1], Flumioxazin [herbicidal compound 2], Cinidon-ethyl [herbicidal compound 3] etc.;

pyridazinone herbicide active compound: Flufenpyr-ethyl [herbicidal compound 4], Brompyrazone [herbicidal compound 5] etc.;

uracil herbicidal active compound: Butafenacil [herbicidal compound 6], Bromacil [herbicidal compound 7], Flupropacil [herbicidal compound 8], Benzofendizone [herbicidal compound 9] etc.;

triazolone herbicidal active compound: Carfentrazone-ethyl [herbicidal compound 10], Sulfentrazone [herbicidal compound 11] etc.;

diphenyl ether herbicidal active compound: Lactofen [herbicidal compound 12], Bifenox [herbicidal compound 13], Chlornitrophenone [herbicidal compound 14], Chlomethoxynil [herbicidal compound 15] etc.;

sulfonylurea herbicidal active compound: Sulfosulfuron [herbicidal compound 16], Imazosulfuron [herbicidal compound 17], Nicosulfuron [herbicidal compound 18], Primisulfuron-methyl [herbicidal compound 19], Rimsulfuron [herbicidal compound 20], Halosulfuron-methyl [herbicidal compound 21], Prosulfuron [herbicidal compound 22], Thifensulfuron-methyl [herbicidal compound 23] etc.;

phenoxypropionic acid herbicidal active compound: Cloazifop [herbicidal compound 24], Diclofop [herbicidal compound 25], Fluazifop [herbicidal compound 26], etc.;

triazolopyrimidine herbicidal active compound: Diclosulam [herbicidal compound 27], Cloransulam [herbicidal compound 28], Flumetsulam [herbicidal compound 29], Penoxsulam [herbicidal compound 30], Pyloxsulam [herbicidal compound 31], Metosulam [herbicidal compound 32] etc.;

anilide herbicidal active compound: Picolinafen [herbicidal compound 33], Flufenacet [herbicidal compound 34], Mefenacet [herbicidal compound 35] etc.;

triazine herbicidal active compound: Atrazin [herbicidal compound 36], Metribuzin [herbicidal compound 37] etc.;

urea herbicidal active compound: Fluometuron [herbicidal compound 38], Isoproturon [herbicidal compound 39], Dymron [herbicidal compound 40] etc.;

imidazoline herbicidal active compound: Imazapyr [herbicidal compound 41], Imazaquin [herbicidal compound 42], Imazethapyr [herbicidal compound 43] etc.;

chloroacetamide herbicidal active compound: Pretilachlor [herbicidal compound 44], Butachlor [herbicidal compound 45] etc.;

thiolcarbamate herbicidal active compound: Benthiocarb [herbicidal compound 46], Esprocarb [herbicidal compound 47], Molinate [herbicidal compound 48] etc.;

amide herbicidal active compound: bromobutide [herbicidal compound 49], Propanil [herbicidal compound 50], Cafenstrole [herbicidal compound 51] etc.;

benzoylpyrazole herbicidal active compound: Pyrazoxyfen [herbicidal compound 52], Benzofenap [herbicidal compound 53] etc.; and methyl{2-chloro-4-fluoro-5-[5,6,7,8-tetrahydro-3-oxo-1H,3H-[1,3,4]thiadiazolo[3,4-a]pyridazin-1-ylideneamino]phenylthio}acetate [herbicidal compound 54], N-benzyl-2-(α,α,α,4-tetrafluoro-m-tolyloxy)butylamide [herbicidal compound 55], and 2-(2,4-dichloro-5-prop-2-ynyloxyphenyl)-5,6,7,8-tetrahydro-1,2,4-triazolo[4,3-a]pyridine-3(2H)-one [herbicidal compound 56].

As the fungicidal active compound, examples include azole fungicidal active compound: Propiconazole [fungicidal compound 1], Triadimenol [fungicidal compound 2], Prochloraz [fungicidal compound 3], Penconazole [fungicidal compound 4], Tebuconazole [fungicidal compound 5], Flusilazole [fungicidal compound 6], Diniconazole [fungicidal compound 7], Bromconazole [fungicidal compound 8], Epoxyconazole [fungicidal compound 9], Difenoconazole [fungicidal compound 10], Cyproconazole [fungicidal compound 11], Metconazole [fungicidal compound 12], Triflumizole [fungicidal compound 13], Tetraconazole [fungicidal compound 14], Myclobutanil [fungicidal compound 15], Fenbuconazole [fungicidal compound 16], Hexaconazole [fungicidal compound 17], Fluquinconazole [fungicidal compound 18], Trityconazole [fungicidal compound 19], Bitertanol [fungicidal compound 20], Imazalil [fungicidal compound 21], Flutriafol [fungicidal compound 22] etc.;

morpholine fungicidal active compound: Fenpropimorph [fungicidal compound 23], Tridemorph [fungicidal compound 24], Fenpropimorph [fungicidal compound 25], Dimethomorph [fungicidal compound 26] etc.;

benzimidazole fungicidal active compound: Carbendazim [fungicidal compound 27], Benomyl [fungicidal compound 28], Tiabendazole [fungicidal compound 29], Thiophanate-methyl [fungicidal compound 30] etc.;

strobilurin fungicidal active compound: Azoxystrobin [fungicidal compound 31], Trifloxystrobin [fungicidal compound 32], Picoxystrobin [fungicidal compound 33], Pyraclostrobin [fungicidal compound 34], Dimoxystrobin [fungicidal compound 35], Fluoxastrobin [fungicidal compound 36], Metominostrobin [fungicidal compound 37], Orysastrobin [fungicidal compound 38] etc.;

dicarboxyimide fungicidal active compound: Procymidone [fungicidal compound 39], Iprodione [fungicidal compound 40], Vinclozolin [fungicidal compound 41] etc.;

carboxyamide fungicidal active compound: Furametpyr [fungicidal compound 42], Mepronil [fungicidal compound 43], Flutolanil [fungicidal compound 44], Trifluzamide [fungicidal compound 45] etc.;

anilinopyrimidine fungicidal active compound: Cyprodinil [fungicidal compound 46], Pyrimethanil [fungicidal compound 47], Mepanipyrim [fungicidal compound 48] etc.;

phenylpyrrole fungicidal active compound: Fenpiclonil [fungicidal compound 49], Fludioxonil [fungicidal compound 50] etc.;

carbamate fungicidal active compound: Iprovalicarb [fungicidal compound 51], Benthiavalicarb [fungicidal compound 52], Diethofencarb [fungicidal compound 53] etc.;

pyridine fungicidal active compound: Boscalid [fungicidal compound 54], Fluazinam [fungicidal compound 55] etc.; and (Z)-2'-methylacetophenone 4,6-dimethylpyrimidin-2-ylhydrazone, 1-(methoxycarbonyl)=2-(1-methylethyl)-4-(2,6-dichlorophenyl)-5-amino-1H-pyrazole-3-one [fungicidal compound 56], 1-[(ethylthio)carbonyl]-2-(1-methylethyl)-4-(2,6-dichlorophenyl)-5-amino-1H-pyrazole-3-one [fungicidal compound 57], 1-[(2-propenylthio)carbonyl]-2-(1-methylethyl)-4-(2-methylphenyl)-5-amino-1H-pyrazole-3-one [fungicidal compound 58], 5-methyl-1,2,4-triazolo-[3,4-b][1,3]benzothiazole [fungicidal compound 59], and 1,2,5,6-tetrahydropyrrolo[3,2,1-ij]quinoline-4-one, 3-allyloxy-1,2-benzothiazole 1,1-dioxide [fungicidal compound 60].

As the insecticidal (acaricidal) active compound, examples includes organic phosphorus insecticidal active compound: Fenitrothion [insecticidal compound 1], Diazinon [insecticidal compound 2], Chlorpyrifos [insecticidal compound 3] etc.;

carbamate insecticidal active compound: Benfuracarb [insecticidal compound 4], Propoxur [insecticidal compound 5], Carbosulfan [insecticidal compound 6], Carbaryl [insecticidal compound 7], Aldicarb [insecticidal compound 8], Fenothiocarb [insecticidal compound 9] etc.;

pyrethroid insecticidal active compound: Etofenprox [insecticidal compound 10], Fenvalerate [insecticidal compound 11], Esfenvalerate [insecticidal compound 12], Fenpropathrin [insecticidal compound 13], Cypermethrin [insecticidal compound 14], Permethrin [insecticidal compound 15], Cyhalothrin [insecticidal compound 16], Deltamethrin [insecticidal compound 17], Cycloprothrin [insecticidal compound 18], Fluvalinate [insecticidal compound 19], Bifenthrin [insecticidal compound 20], Halfenprox [insecticidal compound 21], Tralomethrin [insecticidal compound 22], Silafluofen [insecticidal compound 23], d-Phenothrin [insecticidal compound 24], Cyphenothrin [insecticidal compound 25], d-Resmethrin [insecticidal compound 26], Acrinathrin [insecticidal compound 27], Cyfluthrin [insecticidal compound 28], Tefluthrin [insecticidal compound 29], Transfluthrin [insecticidal compound 30], Tetramethrin [insecticidal compound 31], Allethrin [insecticidal compound 32], Prallethrin [insecticidal compound 33], Enpenthrin [insecticidal compound 34], Imiprothrin [insecticidal compound 35], d-Furamethrin [insecticidal compound 36] etc.;

nicotinoid insecticidal active compound: Clothianidin [insecticidal compound 37], Imidacloprid [insecticidal compound 38], Thiamethoxiam [insecticidal compound 39], Thiacloprid [insecticidal compound 40] etc.;

benzoylphenylurea insecticidal active compound: Chlorfluazuron [insecticidal compound 41], Teflubenzuron [insecticidal compound 42], Flufenoxuron [insecticidal compound 43], Bistrifluron [insecticidal compound 44], Buprofezin [insecticidal compound 45], Triflumuron [insecticidal compound 46] etc.;

pyrazole insecticidal active compound: Acetoprole [insecticidal compound 47], Ethiprole [insecticidal compound 48], Fipronil [insecticidal compound 49], Pyraclofos [insecticidal compound 50] etc.;

juvenile hormone insecticidal active compound: Pyriproxyfen [insecticidal compound 51], Fenoxycarb [insecticidal compound 52] etc.; and (RS)-5-tertiarybutyl-2-[2-(2,6-dufluorophenyl)-4,5-dihydro-1,3-oxazol-4-yl]phenetole [insecticidal compound 53], and 2,6-dichloro-4-(3,3-dichloroallyloxy)phenyl 3-[5-(trifluoromethyl)-2-pyridyloxy]propyl ether [insecticidal compound 54].

As the plant growth controlling compound, examples include an azole plant growth controlling compound: Uniconazole-P [plant growth controlling compound 1], Paclobutrazol [plant growth controlling compound 2] etc.; and (RS)-4'-chloro-2'-(α-hydroxybenzyl)isonicotineanilide [plant growth controlling compound 3].

The above-described agrochemical active compounds are compounds described in the known literature such as The Pesticide Manual, 13$^{th}$ edition (published by The British Crop Protection Council in 1987) or the like.

The present liquid agrochemical composition can contain one or more kinds of hydrophobic agrochemical active compounds and, in the present liquid agrochemical composition, a total amount of hydrophobic agrochemical active compounds is in a range of 0.5 to 30% by weight, preferably 0.5 to 25% by weight.

In the present liquid agrochemical composition, even in the case of a solid hydrophobic agrochemical active compound which is hardly soluble in an aromatic hydrocarbon solvent (specifically solubility in xylene at 25° C. is not higher than 10 g/L), a liquid agrochemical preparation having a practical concentration can be prepared.

In the present invention, the nonionic surfactant selected from the group (A) (hereinafter, referred to as present nonionic surfactant) may be used alone or in a combination thereof and, in the present liquid agrochemical composition, a total amount of the present nonionic surfactant is in a range of 1 to 20% by weight, preferably 1 to 15% by weight, further preferably 1 to 12% by weight.

In the present nonionic surfactant, it is preferable that p:q is in a range of 1:0.5 to 2.0 in a partial structure —$(CH_2CH_2O)_p$ derived from a polyoxyethylene structure, and a partial structure $(CH(CH_3)CH_2O)_q$ derived from a polyoxypropylene structure.

In the present invention, preferably, the present nonionic surfactant is a polyoxyethylene polyoxypropylene block copolymer.

As the polyoxyethylene polyoxypropylene block copolymer, a commercially available surfactant such as Teric PE 64 (manufactured by Huntsman) can be used.

As the polyoxyethylene polyoxypropylene alkyl ether, a commercially available surfactant such as Antarox BO/327 (all manufactured by Rhodia Nicca) can be used.

In the present invention, the anionic surfactant is, for example, an anionic surfactant selected from the following group (B), and may be used alone or in a combination thereof. In the present liquid agrochemical composition, a total amount of the present anionic surfactant is in a range of 0 to 10% by weight, preferably 0 to 8% by weight, further preferably 1 to 7% by weight, the group (B):
arylsulfonate such as dodecylbenzenesulfonate etc,
polyoxyethylene (poly)arylaryl ether sulfate such as polyoxyethylene distyryl phenyl ether sulfate etc,
polyoxyethylene (poly)arylaryl ether phosphate such as polyoxyethylene tristyryl phenyl ether phosphoric acid etc,
polyoxyethylene alkylarylphosphate, and
polyoxyethylene alkylphosphate.

In general, examples of the salt of the sulfonate, the sulfate, and the phosphate include a sodium salt, a potassium salt, and an ammonium salt.

The amount of γ-butyrolactone contained in the present liquid agrochemical composition is in a range of 6 to 60% by weight, preferably 15 to 60% by weight.

The amount of 1,3-dimethyl-2-imidazolidinone contained in the present liquid agrochemical composition is a range of 20 to 75% by weight, preferably 25 to 50% by weight.

In the present invention, as γ-butyrolactone and 1,3-dimethyl-2-imidazolidinone, commercially available ones can be used.

In the present liquid agrochemical composition, a weight ratio of γ-butyrolactone and 1,3-dimethyl-2-imidazolidinone is preferably in a range of 10:90 to 50:50. In addition, 1,3-dimethyl-2-imidazolidinone is usually not less than 1.5 parts by weight relative to 1 part by weight of the hydrophobic agrochemical active compound.

Specific examples of the liquid agrochemical composition are as follows:

A liquid agrochemical composition comprising
  a hydrophobic agrochemical active compound 0.5 to 30% by weight,
  a polyoxyethylene polyoxypropylene block copolymer 1 to 20% by weight,
  an anionic surfactant 0 to 10% by weight,
  γ-butyrolactone 6 to 60% by weight, and
  1,3-dimethyl-2-imidazolidinone 20 to 75% by weight;

A liquid agrochemical composition comprising
  a hydrophobic agrochemical active compound 0.5 to 30% by weight,
  a polyoxyethylene polyoxypropylene block copolymer 1 to 20% by weight,
  an anionic surfactant 0 to 10% by weight,
  γ-butyrolactone 6 to 60% by weight, and
  1,3-dimethyl-2-imidazolidinone 20 to 75% by weight,
  wherein a weight ratio of γ-butyrolactone and 1,3-dimethyl-2-imidazolidinone is a range of 10:90 to 50:50, and 1,3-dimethyl-2-imidazolidinone is not less than 1.5 parts by weight relative to 1 part by weight of the hydrophobic agrochemical active compound;

A liquid agrochemical composition comprising
  a hydrophobic agrochemical active compound 0.5 to 30% by weight,
  a nonionic surfactant selected from the group (A) 1 to 15% by weight,
  an anionic surfactant 0 to 8% by weight,
  γ-butyrolactone 15 to 60% by weight, and
  1,3-dimethyl-2-imidazolidinone 25 to 50% by weight; and A liquid agrochemical composition comprising
  a hydrophobic agrochemical active compound 0.5 to 25% by weight,
  a polyoxyethylene polyoxypropylene block copolymer 1 to 15% by weight,
  an anionic surfactant 0 to 8% by weight,
  γ-butyrolactone 15 to 60% by weight, and
  1,3-dimethyl-2-imidazolidinone 25 to 50% by weight.

The present liquid agrochemical composition may contain one or more adjuvant for a preparation such as antioxidants, coloring agents, flavors, efficacy enhancers, drug-induced sufferings-alleviating agents and the like, if necessary.

Examples of the antioxidant include 3-/2-t-butyl-4-hydroxyanisole, butylated hydroxytoluene, and the like, and examples of the coloring agent include Rhodamine B, Yellow No. 4, Blue No. 1, Red No. 2, and the like.

In the present liquid agrochemical composition, a total amount of the preparation adjuvant is in a range of 0 to 5% by weight.

The present liquid agrochemical composition can be produced, for example, by adding a hydrophobic agrochemical active compound, the present nonionic surfactant and, if necessary, an anionic surfactant and a adjuvant for a preparation to a mixed solvent of γ-butyrolactone and 1,3-dimethyl-2-imidazolidinone, if necessary with heating (not higher than 80° C.), stirring the mixture until it becomes a uniform solution and, if necessary, filtering the solution.

The present liquid agrochemical composition is a uniform liquid substantially formed from one continuous phase.

The present liquid agrochemical composition is used by diluting with water. The present liquid agrochemical composition can be diluted with water in an amount, usually, a 10 to 10,000-fold, preferably 20 to 5,000-fold amount of water relative to the liquid agrochemical composition. In general, water to be used may be hard water (water having a large content of calcium ion and/or magnesium ion; a total amount of a calcium ion and a magnesium ion in water is expressed as a hardness in ppm of corresponding carbonate) or soft water (water having a small content of calcium ion and/or magnesium ion), or may be water to which an adjuvant such as a spreading agent, an inorganic salt and the like is optionally added.

In a water-diluted solution obtained by diluting the present liquid agrochemical composition with a 10 to 10,000-fold amount of water (hereinafter, referred to as the present water-diluted solution), the hydrophobic agrochemical active compound is solubilized in water with the present nonionic surfactant, or liquid droplets containing the hydrophobic agrochemical active compound have a sufficiently small particle diameter, thus, appearance thereof is greatly different from that of a water-diluted solution of a conventional agrochemical emulsion. That is, the present water-diluted solution containing no coloring component has transparent or pale bluish transparent appearance.

For example, an absorbance measured with transmitted light at a wavelength of 550 nm immediately after dilution of the liquid agrochemical composition with a 100-fold amount of water is usually in a range of 0.001 to 1, while an absorbance of a water-diluted solution of a conventional agrochemical emulsion under the same conditions is larger than 2, from which the present liquid agrochemical composition can be discriminated from a conventional agrochemical emulsion. For analyzing the absorbance, an ultraviolet and visible spectrophotometer (e.g. Model UV-2500 PC type manufactured by Shimadzu Corporation) can be used.

Hereinafter, the present invention will be explained in more detail by way of Examples, Test Examples, and the like, but the present invention is not limited to these Examples.

Example 1

At 20° C., a fungicidal compound 58 (5.00 g in terms of active ingredient), calcium dodecylbenzenesulfonate (4.00 g manufactured by Huntsman), a polyoxyethylene polyoxypropylene block copolymer (4.50 g, manufactured by Stepan) and 1,3-dimethyl-2-imidazolidinone (35.0 g) were weighed in a 100 ml measuring flask, the total volume was adjusted to 100 ml with γ-butyrolactone, and the mixture was stirred until it became a uniform solution to obtain the present liquid agrochemical composition (hereinafter, referred to as the present solution 1).

Example 2

At 20° C., an insecticidal compound 37 (5.00 g in terms of active ingredient), calcium dodecylbenzenesulfonate (3.00 g manufactured by Huntsman), a polyoxyethylene polyoxypropylene block copolymer (3.00 g, manufactured by Stepan) and 1,3-dimethyl-2-imidazolidinone (35.0 g) were weighed in a 100 ml measuring flask, the total volume was adjusted to 100 ml with γ-butyrolactone, and the mixture was stirred until it became a uniform solution to obtain the present liquid agrochemical composition (hereinafter, referred to as the present solution 2).

Example 3

At 20° C., an insecticidal compound 37 (5.00 g in terms of active ingredient), a polyoxyethylene polyoxypropylene block copolymer (3.00 g, manufactured by Stepan) and 1,3-dimethyl-2-imidazolidinone (45.0 g) were weighed in a 100 ml measuring flask, the total volume was adjusted to 100 ml with γ-butyrolactone, and the mixture was stirred until it became a uniform solution to obtain the present liquid agrochemical composition (hereinafter, referred to as the present solution 3).

Example 4

At 20° C., an insecticidal compound 37 (5.00 g in terms of active ingredient), a polyoxyethylene polyoxypropylene block copolymer (3.00 g, manufactured by Stepan) and 1,3-dimethyl-2-imidazolidinone (55.0 g) were weighed in a 100 ml measuring flask, the total volume was adjusted to 100 ml with γ-butyrolactone, and the mixture was stirred until it became a uniform solution to obtain the present liquid agrochemical composition (hereinafter, referred to as the present solution 4).

Example 5

At 20° C., an insecticidal compound 37 (5.00 g in terms of active ingredient), a polyoxyethylene polyoxypropylene block copolymer (3.00 g, manufactured by Stepan) and 1,3-dimethyl-2-imidazolidinone (65.0 g) were weighed in a 100 ml measuring flask, the total volume was adjusted to 100 ml with γ-butyrolactone, and the mixture was stirred until it became a uniform solution to obtain the present liquid agrochemical composition (hereinafter, referred to as the present solution 5).

Example 6

At 20° C., an insecticidal compound 37 (5.00 g in terms of active ingredient), a polyoxyethylene polyoxypropylene block copolymer (3.00 g, manufactured by Stepan) and 1,3-dimethyl-2-imidazolidinone (75.0 g) were weighed in a 100 ml measuring flask, the total volume was adjusted to 100 ml with γ-butyrolactone, and the mixture was stirred until it became a uniform solution to obtain the present liquid agrochemical composition (hereinafter, referred to as the present solution 6).

Test Example 1

Into a 100 ml measuring cylinder with a stopper was placed 99 ml of CIPAC standard water D (342 ppm), and a temperature was maintained in a constant temperature water bath at 30° C. for a while. Then, 1 ml of each of the present solutions 1 to 6 was added to the measuring cylinder, the measuring cylinder was inverted 10 times at a ratio of one time per 2 seconds, and a temperature was maintained again in a constant temperature water bath at 30° C. for 30 minutes. Thereafter, the state of a diluted solution in each measuring cylinder was observed, and it was found that all retained the stable state, and had transparent appearance.

Example 7

At 20° C., a herbicidal compound 2 (5.00 g in terms of active ingredient), a polyoxyethylene polyoxypropylene block copolymer (15.00 g, manufactured by Stepan), 1,3-dimethyl-2-imidazolidinone (67.0 g) and γ-butyrolactone (15.0 g) were weighed, and the mixture was stirred until it became a uniform solution to obtain the present liquid agrochemical composition (hereinafter, referred to as the present solution 7).

Comparative Example 1

At 20° C., a herbicidal compound 2 (3.00 g in terms of active ingredient), polyoxyethylene sorbitan monolaurate (15.00 g, manufactured by Rhodia Nicca), 1,3-dimethyl-2-imidazolidinone (67.0 g) and γ-butyrolactone (15.0 g) were weighed, and the mixture was stirred until it became a uniform solution to obtain comparative solution (hereinafter, referred to as the comparative solution 1).

Test Example 2

Into a 100 ml measuring cylinder with a stopper was placed 99 ml of CIPAC standard water D (342 ppm), and a temperature was maintained in a constant temperature water bath at 30° C. for a while. Then, 1 ml of each of the present solution 7 and comparative solution 1 was added to the measuring cylinder, the measuring cylinder was inverted 10 times at a ratio of one time per 2 seconds, and a temperature was maintained again in a constant temperature water bath at 30° C. for 2 hours. Thereafter, the state of a diluted solution in each measuring cylinder was observed, and it was found that the present solution 7 retained the stable state, and had pale bluish transparent appearance. On the other hand, in comparative solution 1, a large amount of crystals deposited on the bottom of the measuring cylinder was observed.

As described hereinabove, the liquid agrochemical composition of the present invention has a very stable water-diluted state, and is useful as a preparation containing an agrochemical active compound.

What is claimed is:

1. A liquid agrochemical composition consisting of:
   0.5 to 30% by weight of one or more hydrophobic agrochemical active compounds;
   1 to 20% by weight of one or more nonionic surfactants selected from the following group (A);
   0 to 10% by weight of one or more anionic surfactants;
   6 to 60% by weight of γ-butyrolactone;
   20 to 75% by weight of 1,3-dimethyl-2-imidazolidinone; and
   0 to 5% by weight of one or more preparation adjuvants selected from the group consisting of antioxidants, coloring agents and flavors;
   the group (A):
   polyoxyethylene polyoxypropylene block copolymer,
   polyoxyethylene polyoxypropylene alkyl ether,
   polyoxyethylene polyoxypropylene alkyl phenol,
   polyoxyethylene polyoxypropylene polystyryl phenyl ether, and
   polyoxyethylene polyoxypropylene castor oil.

2. The liquid agrochemical composition according to claim 1, wherein the nonionic surfactant is a polyoxyethylene polyoxypropylene block copolymer.

3. The liquid agrochemical composition according claim 1, wherein an amount of the anionic surfactant is in a range of 1 to 10% by weight.

4. The liquid agrochemical composition according to claim 3, wherein the anionic surfactant is an alkylbenzenesulfonate.

5. A water-diluted solution, which is obtained by diluting the liquid agrochemical composition according to claim 1 with a 10 to 10,000-fold amount of water.

* * * * *